US011273282B2

(12) United States Patent
Leonard et al.

(10) Patent No.: US 11,273,282 B2
(45) Date of Patent: Mar. 15, 2022

(54) VAPOR TRANSFER CARTRIDGE

(71) Applicant: Vapotherm, Inc., Exeter, NH (US)

(72) Inventors: Scott A. Leonard, Bedford, NH (US);
Michael J. Webb, Hollis, NH (US);
Martin Stillig, Dransfeld (DE)

(73) Assignee: Vapotherm, Inc., Exeter, NH (US)

( * ) Notice: Subject to any disclaimer, the term of this patent is extended or adjusted under 35 U.S.C. 154(b) by 1317 days.

(21) Appl. No.: 15/298,712

(22) Filed: Oct. 20, 2016

(65) Prior Publication Data

US 2018/0110956 A1    Apr. 26, 2018

(51) Int. Cl.
*A61M 16/14* (2006.01)
*B01F 3/02* (2006.01)
(Continued)

(52) U.S. Cl.
CPC ...... *A61M 16/145* (2014.02); *A61M 16/0096* (2013.01); *A61M 16/0666* (2013.01);
(Continued)

(58) Field of Classification Search
CPC ............... A61M 16/145; A61M 16/16; A61M 16/0096; A61M 16/0666; A61M 16/162; A61M 2205/121; A61M 2207/10; Y10S 261/65; Y10S 165/907; Y10S 55/17; B01D 63/02; B01D 2313/21; B01D 2313/44; B01D 2313/08; B01D 2313/12;
(Continued)

(56) References Cited

U.S. PATENT DOCUMENTS

| | | | | |
|---|---|---|---|---|
| 1,899,106 | A * | 2/1933 | Richter | D21D 5/02 8/156 |
| 2,073,991 | A * | 3/1937 | Koser | B01D 29/05 210/445 |
| 3,170,873 | A * | 2/1965 | May | B01D 17/10 210/307 |

(Continued)

FOREIGN PATENT DOCUMENTS

| | | |
|---|---|---|
| EP | 3025775 A1 | 6/2016 |
| WO | WO-2005097307 A1 | 10/2005 |

(Continued)

OTHER PUBLICATIONS

International Search Report and Written Opinion for International Application No. PCT/US2017/057096 dated Feb. 7, 2018 (12 pages).

(Continued)

*Primary Examiner* — Victoria Murphy
(74) *Attorney, Agent, or Firm* — White & Case LLP

(57) ABSTRACT

Systems, methods, and devices are disclosed for manufacturing a vapor transfer cartridge with a constant inner diameter to maximize the area available for fibers required for heating and humidifying a breathing gas. In one aspect, a vapor transfer cartridge includes a center tube extending along a first axis from a first to a second end, having a continuous inner diameter, a first header piece configured as a cap and including a channel about an inner circumference of the header piece coupled to the first end of the center tube, a second header piece coupled to the second end of the center tube, and a plurality of fibers arranged along the axis of the center tube from the first end to the second end. The first header piece further includes a first port, and a baffle.

21 Claims, 9 Drawing Sheets

(51) Int. Cl.
  *B01F 5/04* (2006.01)
  *A61M 16/16* (2006.01)
  *A61M 16/00* (2006.01)
  *A61M 16/06* (2006.01)
(52) U.S. Cl.
  CPC .......... *A61M 16/16* (2013.01); *A61M 16/162* (2013.01); *B01F 3/022* (2013.01); *B01F 5/0476* (2013.01); *A61M 2205/121* (2013.01); *A61M 2207/10* (2013.01)
(58) Field of Classification Search
  CPC ...... B01D 69/08; B01D 63/021; B01D 63/04; B01D 53/22; B01D 63/026; B01D 65/00; B01D 2313/20; B01D 61/18; B01D 63/022; B01D 63/046; B01D 2313/04; B01D 2313/10; B01D 2313/105; B01D 2313/38; B01D 2319/04; B01D 2321/04; B01D 2321/2066; B01D 2321/26; B01D 46/10; B01D 53/261; B01D 53/266; B01D 61/30; B01D 63/024; B01D 65/02; B01D 17/045; B01D 17/10; B01D 19/0031; B01D 2253/104; B01D 2253/106; B01D 2253/11; B01D 2253/20; B01D 2253/304; B01D 2253/34; B01D 2257/206; B01D 2257/702; B01D 2257/80; B01D 2258/0258; B01D 2259/4541; B01D 2259/455; B01D 2313/086; B01D 2313/125; B01D 2313/42; B01D 2313/90; B01D 2319/06; B01D 29/05; B01D 46/02; B01D 53/0415; B01D 53/0431; B01D 53/323; B01D 63/025; B01D 63/027; B01D 67/0041; B01D 69/085; B01D 69/088; B01D 71/02; B01F 3/022; B01F 5/0476
  See application file for complete search history.

(56) References Cited

U.S. PATENT DOCUMENTS

| | | | | |
|---|---|---|---|---|
| 3,846,518 A * | 11/1974 | McPhee | F16L 41/02 | 261/123 |
| 3,870,470 A * | 3/1975 | Yoshida | B01F 5/0688 | 422/46 |
| 3,882,024 A * | 5/1975 | Holmes | B01D 63/02 | 210/321.8 |
| 3,957,648 A * | 5/1976 | Roget | B01D 53/22 | 210/321.88 |
| 4,038,190 A * | 7/1977 | Baudet | B01D 46/02 | 210/321.81 |
| 4,082,670 A * | 4/1978 | Joh | B01D 63/02 | 210/195.2 |
| 4,125,468 A * | 11/1978 | Joh | B01D 63/02 | 210/321.8 |
| 4,219,426 A * | 8/1980 | Spekle | B01D 63/02 | 210/232 |
| 4,268,278 A * | 5/1981 | Dobo | D01D 5/24 | 419/2 |
| 4,334,993 A * | 6/1982 | Norton | B01D 63/022 | 165/83 |
| 4,376,095 A * | 3/1983 | Hasegawa | A61M 1/1698 | 422/46 |
| 4,430,994 A | 2/1984 | Clawson et al. | | |
| 4,464,186 A * | 8/1984 | Mann | B01D 46/10 | 210/446 |
| D288,129 S | 2/1987 | Taylor | | |
| 4,698,207 A * | 10/1987 | Bringham | A61M 1/1698 | 128/DIG. 3 |
| 4,876,012 A * | 10/1989 | Kopp | B01D 61/18 | 210/644 |
| 4,957,516 A * | 9/1990 | Daniels | B01D 46/10 | 55/323 |
| 5,002,668 A * | 3/1991 | Spranger | B01D 63/02 | 210/321.79 |
| D322,124 S | 12/1991 | Lichte et al. | | |
| 5,084,244 A * | 1/1992 | Muramoto | A61M 1/1698 | 128/DIG. 3 |
| 5,094,750 A * | 3/1992 | Kopp | B01D 61/18 | 210/321.81 |
| 5,234,591 A * | 8/1993 | Darnell | B01D 53/22 | 210/321.81 |
| 5,993,612 A * | 11/1999 | Rostaing | B01D 53/323 | 204/158.2 |
| 6,183,639 B1 * | 2/2001 | de Winter | B01D 63/02 | 210/321.79 |
| 6,224,763 B1 * | 5/2001 | Feng | B01D 61/00 | 210/232 |
| 6,493,883 B2 | 12/2002 | Jones | | |
| 6,551,291 B1 * | 4/2003 | de Juan, Jr. | A61F 9/00727 | 604/289 |
| 6,616,735 B1 * | 9/2003 | Burban | B01D 53/268 | 95/52 |
| D492,772 S | 7/2004 | Austin | | |
| D569,008 S | 5/2008 | Lundqvist et al. | | |
| D640,786 S | 6/2011 | Sato et al. | | |
| D640,896 S | 7/2011 | Molayem | | |
| D676,567 S | 2/2013 | van den Engh | | |
| D705,423 S | 5/2014 | Walsh Cutler | | |
| 8,857,429 B2 | 10/2014 | Spandorfer | | |
| D735,880 S | 8/2015 | Bargh et al. | | |
| 9,114,225 B1 * | 8/2015 | Roberts | A61M 16/145 | |
| D765,836 S | 9/2016 | Kammer et al. | | |
| D803,394 S | 11/2017 | Hamel et al. | | |
| D804,653 S | 12/2017 | Clark et al. | | |
| D805,193 S | 12/2017 | Shoji et al. | | |
| D833,004 S | 11/2018 | Leonard | | |
| D861,863 S | 10/2019 | Leonard | | |
| 10,596,345 B2 | 5/2020 | Leonard | | |
| 2001/0048198 A1 * | 12/2001 | Dulin | B65D 35/44 | 277/316 |
| 2002/0069869 A1 | 6/2002 | Farmer | | |
| 2003/0008389 A1 | 1/2003 | Carll | | |
| 2003/0168062 A1 * | 9/2003 | Blythe | A61M 15/0086 | 128/203.12 |
| 2004/0245658 A1 * | 12/2004 | Niland | B01F 5/0476 | 261/104 |
| 2005/0039746 A1 | 2/2005 | Grychowski et al. | | |
| 2005/0247201 A1 * | 11/2005 | Arno | B01D 53/261 | 96/134 |
| 2009/0137920 A1 | 5/2009 | Colman et al. | | |
| 2010/0059053 A1 | 3/2010 | Niland | | |
| 2010/0305446 A1 * | 12/2010 | Berard-Anderson | A61M 5/16886 | 600/454 |
| 2012/0137879 A1 * | 6/2012 | Taylor | B01D 63/027 | 95/46 |
| 2016/0058968 A1 | 3/2016 | Yatsevich et al. | | |
| 2016/0184547 A1 * | 6/2016 | Leonard | A61M 16/20 | 128/203.25 |
| 2020/0246577 A1 | 8/2020 | Leonard | | |

FOREIGN PATENT DOCUMENTS

| | | |
|---|---|---|
| WO | WO-2007038152 A2 | 4/2007 |
| WO | WO-2009022004 A2 | 2/2009 |
| WO | WO-2009045198 A1 | 4/2009 |
| WO | WO-2016109294 A1 | 7/2016 |
| WO | WO-2016110321 A1 | 7/2016 |

OTHER PUBLICATIONS

International Search Report and Written Opinion for International Application No. PCT/US2015/067146 dated Oct. 26, 2016 (18 pages).

* cited by examiner

VAPOR TRANSFER CARTRIDGE

BACKGROUND

Patients with respiratory ailments may be treated with respiratory assist devices, for example, devices that deliver supplemental breathing gas to a patient. Such devices may deliver gas to a patient using high flow therapy (HFT). HFT devices deliver a high flow rate of breathing gas to a patient via an interface such as a nasal cannula to increase a patient's fraction of inspired oxygen (FiO2), decrease a patient's work of breathing, or to do both. One category of these devices uses membranes to humidify the gasses delivered to the patient. Specifically, gas (e.g., oxygen) is humidified by passing the gas through fibers with membranes within a vapor transfer cartridge that is filled with liquid (e.g., water). The membrane may be permeable to gas, but impermeable to liquid. Thus, water vapor is permitted to permeate the membrane, while liquid water is not. The efficiency of humidification of the gas is dependent on the surface area of the membranes.

The need to optimize available fiber surface area must be balanced with size and geometric constraints of the vapor transfer cartridges that house the fibers, as patient comfort considerations and pre-existing systems prohibit simply increasing the size of the cartridges to allow for more fibers. Additionally, a molded single-piece vapor transfer cartridge is not able to have a constant inner diameter because tooled pieces require an increasing diameter from the center of the piece in order to prevent the tools from becoming trapped. Thus, the minimized inner cross-sectional area limits the number and size of the fibers that can be contained in the cartridge. Further compounding the space constraints is the need to blunt and direct the force of water fed into the vapor transfer cartridge. For example, as water is fed into the housing at a pressure and direction necessary to ensure its circulation, the fibers adjacent to the point of entry of the water may become damaged if the water pressure is too high. One technique of blunting the water is to include internal baffles in the vapor transfer cartridge designed to partially block or disperse water at an inlet port, which may further limit the cross-sectional area of the vapor transfer cartridge at various points. As the inner cross-sectional area drops, fewer fibers are able to fit in the constrained vapor transfer cartridges and the rate of humidification suffers as a result.

Further, the manufacture of vapor transfer cartridges as a single extrusion can result in difficulty attaining a precise length of the cartridge and creation of desired features may be impossible. For example, the creation of ports for gas and water on the side wall of the cartridge is not possible when the cartridge is manufactured as a single extruded unit. As a result, ports must be added after manufacture of the cartridge leading to increased manufacture expense, or alternative manufacturing options must be considered. Inaccurately sized cartridges may not fit onto pre-existing couplings on gas heating and humidification therapy units at the predetermined positions, resulting in additional manufacture costs or necessitating redesign of existing systems.

SUMMARY

Accordingly, disclosed herein are systems, methods, and devices for manufacture and assembly of a vapor transfer cartridge that allows a maximum number of fibers to be fit into the cartridge for use in administration of humidified breathing gas therapies. For example, by manufacturing the vapor transfer cartridge in at least three discrete pieces, with each piece designed to serve particular functions, the inner cross-sectional area of the assembled vapor transfer cartridge is increased. For example, manufacture of a vapor transfer cartridge with three pieces allows creation of a center tube with a constant and maximized inner cross-sectional area. Two header pieces are designed to blunt and direct the force of water fed into the vapor transfer cartridge, while ensuring proper circulation. The maximized number of fibers allows the cartridge to efficiently humidify the gas by providing ample surface area and consistent wetting of the fibers.

Additionally or alternatively, the systems, methods, and devices can be precisely designed to fit existing systems upon assembly. For example, the vapor transfer cartridges can be used in existing capital units that require a specific shape and size because the three-piece manufacturing allows for modular adjustments to precisely align and size the pieces. For example, by separating the center tube from the header, the dimensions of the center tube prior to assembly of the vapor transfer cartridge are less rigid. Furthermore, by designing the header with channel connections, less strict tolerances may be observed. For example, the extruded center tube may "float" within the channel and be bonded at a selected position to obtain a desired length and position. Likewise, the alignment of ports on the vapor transfer cartridge is accomplished by fixturing during assembly to precisely align the ports.

Additionally, designing the header as separate pieces allows for the use of low-profile baffles to be incorporated into the header design at the inlet ports to prevent high water pressure from damaging the fibers, inconsistently wetting the fibers, and properly directing the disbursement of the water throughout the cartridge, while not limiting the number of fibers that can fit into the cartridge. For example, the baffles incorporated into the header design direct the flow of fluid throughout the cartridge and prevent the high pressure water from directly impacting the fibers as it enters the cartridge.

In one aspect, a vapor transfer cartridge includes a center tube, a first header piece, a second header piece, and a plurality of fibers. The center tube extends along a first axis from a first end to a second end and has a continuous inner diameter throughout the length. The continuous inner diameter allows the number of fibers that can fit into the center tube to be maximized for efficient humidification of breathing gas. The first header piece is configured as a cap and is coupled to the first end of the center tube. The first header piece includes a channel about an inner circumference of the header piece, a first port and a baffle. The channel in the header piece enables the center tube to "float" in the channel, allowing less strict tolerances in tube length and allowing various length center tubes to be used. The second header piece is coupled to the second end of the center tube. The plurality of fibers is arranged along the axis of the center tube from the first end to the second end.

A single header piece may include multiple ports and/or multiple ports may be spread among multiple header pieces and end caps. By dispersing the ports to the header pieces and/or end caps, the vapor transfer cartridge may be usable with a variety of capital units, without modifying the center tube. The second header piece can include a second port. The vapor transfer cartridge may include a first end cap coupled to the first header piece and a second end cap coupled to the second header piece. The first end cap includes a third port and the second end cap includes a fourth port. In some implementations, the first port, second port, third port, and fourth port are aligned along a longitudinal axis. Assembling the vapor transfer cartridges from three discrete pieces allows the ports to be precisely aligned and spaced during assembly so that the vapor transfer cartridge ports can be inserted into receiving valves or ports in pre-existing systems. In some implementations, the ports are attached to a water inlet, a water outlet, air inlet, and air outlet on a capital unit. In some implementations, the air inlet is coupled to the first port and provides gas at about eight liters per minute (lpm). In some implementations, the air outlet is coupled to the second port, and the second port provides gas with a humidity within the range of 26-56 mg/L. High gas flow rate and highly humidified gas allow the vapor transfer cartridge to be used with a high flow therapy system.

In some implementations, the channel includes ribs that align and center the center tube. In some implementations, the center tube floats on the ribs to achieve a desired cartridge length. The number of ribs can vary. For example, in some implementations, there are three or more ribs. In some implementations, there are twelve or more ribs.

The baffle may have various shapes to direct the water. For example, based on the shape of the baffle, water may be deflected in a particular angle or at a particular rate. In some implementations, the baffle is a cross-shaped baffle with a dispersing cap. The cross-shaped baffle may allow for water to be deflected at multiple angles. By deflecting the water at multiple angles, water pressure at any single angle, and at an impact point on the fibers, is reduced, preventing damage the fiber. The baffle may extend into the center tube to varying degrees. In some implementations, the baffle extends into the center tube about four mm or less. By extending into the center tube about four mm or less, the risk of snagging the fibers during insertion is reduced. Furthermore, by extending into the center tube about four mm or less, the interior space of the center tube is increased, allowing more fibers to be inserted into the center tube. The baffle design may also aid in ensuring water delivery throughout the center tube. In some implementations, the baffle provides omnidirectional water delivery. Omnidirectional water delivery promotes the travel of water throughout the center tube and consistent wetting of the fibers without damage to fibers near the baffle. To reduce tooling requirements and reduce the manufacturing costs of the center tube, the baffle may be incorporated into a header piece. In some implementations, the baffle is molded with the first header piece, which increases interior space, provides better water deflection, and provides better water delivery. In some implementations, the baffle is flush with the first header piece and can be pushed into an interior cavity of the cartridge after manufacture, increasing interior space for the insertion of fibers. In some implementations, the first header piece and the second header piece each includes a sloped region near the channel, the sloped region centering and guiding the plurality of fibers during assembly.

The fibers may have varying diameters. Furthermore, the diameters of each fiber may be the same or may differ. In some implementations, each fiber in the plurality of fibers has a diameter of about 0.7 mm. A diameter of about 0.7 mm provides ample fiber surface area to efficiently humidify gas passing through the fiber given consistent wetting. In some implementations, the plurality of fibers are porous fibers. In some implementations, the plurality of fibers are non-porous fibers. In some implementations, the plurality of fibers are hollow fiber tubes. In some implementations, the first port includes a barb at an end. The barb may allow the port to engage with a water valve of a pre-existing system.

In another aspect, a method of manufacturing a vapor transfer cartridge includes fitting a first end of a center tube into a first header piece. The center tube has a first end and a second end and a continuous inner diameter to allow a maximum number of fibers to fit inside. The first header piece is a cap with a channel about an inner circumference of the first header piece. The first header piece also includes at least one port on a side of the first header piece and a baffle configured at the port. The method further includes coupling the channel of the first header piece to the first end of the center tube, fitting the second end of the center tube into a second header piece, coupling the channel of the second header piece to the second end of the center tube, and inserting fibers into the center tube through the second header piece.

In some implementations, the method also includes aligning at least one port of the first header piece with at least one port of the second header piece. Aligning the ports allows the vapor transfer cartridge to be fitted to an existing system, provides a comfortable hand position for a handheld device, and/or improves water delivery. In some implementations, placing fibers in the second end of the center tube further comprises placing a number of fibers sufficient to fill the center tube into the second end of the center tube. In some implementations, the number of fibers sufficient to fill the center tube is about 250-700 fibers. In some implementations, the fibers are placed in the second end of the center tube in a hexagonally close packed (HCP) packing structure. In some implementations, the first header piece further comprises a baffle at the at least one port.

Using a center tube and header piece arrangement also provides benefits for securing fibers in the center tube during manufacture. For example, prior to assembling the header piece onto the center tube, the fibers may be more easily inserted into and/or aligned in the center tube. In some implementations, the method also includes injecting a potting material into at least one of the first header piece and the second header piece. During assembly, the potting material may bond the fibers. In some implementations, the method also includes centrifuging the vapor transfer cartridge such that the potting material is deposited at the first side of the center tube adjacent to the first header piece and at the second side of the center tube adjacent to the second header piece. In some implementations, the method also includes coupling a first end cap to an end of the first header piece, and coupling a second end cap to an end of the second header piece. In some implementations, the first end cap includes a gas inlet port and the second end cap includes a gas outlet port.

The disclosed features may be implemented, in any combination and subcombination (including multiple dependent combinations and subcombinations), with one or more other features described herein. The various features described or illustrated above, including any components thereof, may be combined or integrated in other systems. Moreover, certain features may be omitted or not implemented.

BRIEF DESCRIPTION OF THE DRAWINGS

The foregoing and other objects and advantages will be apparent upon consideration of the following detailed description, taken in conjunction with the accompanying drawings, in which like reference characters refer to like parts throughout, and in which.

DETAILED DESCRIPTION

Figure 1:
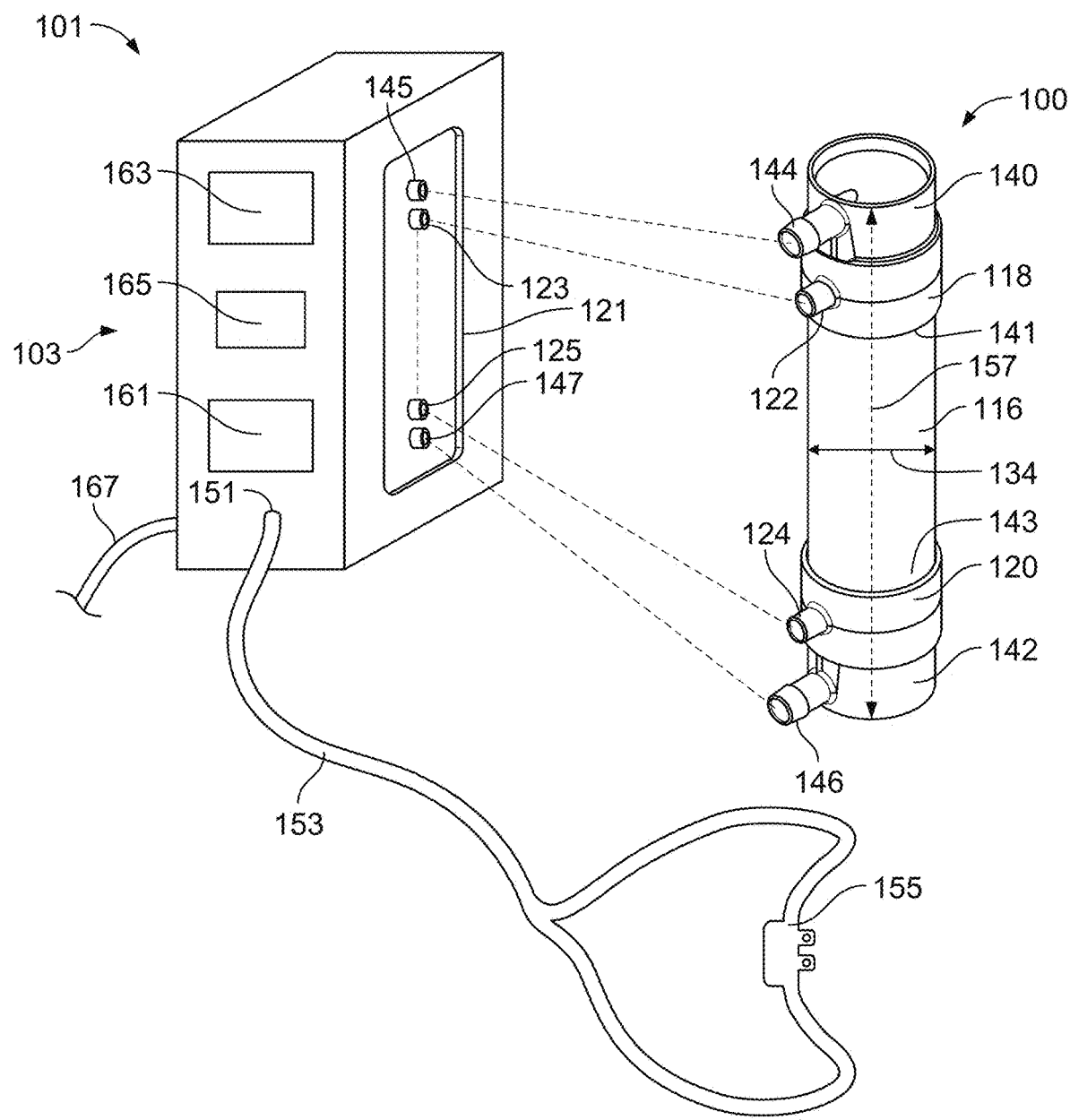
FIG. 1 shows an illustrative respiratory therapy system.

To provide an overall understanding of the systems, devices, and methods described herein, certain illustrative embodiments will be described. Although the embodiments and features described herein are specifically described for use in connection with a high flow therapy (HFT) system, it will be understood that all the components and other features outlined below may be combined with one another in any suitable manner and may be adapted and applied to other applications that require the heating and/or humidifying of a gas, such as manufacture of a dialyzer. Further, the heated and humidified gas described herein is described for use with HFT and with distribution to a patient through a cannula, but it will be understood that the humidified gas may be used in any suitable type of respiratory therapy and with any suitable respiratory therapy devices, including low flow oxygen therapy, continuous positive airway pressure therapy (CPAP), mechanical ventilation, oxygen masks, Venturi masks, and tracheotomy masks.

The systems, methods, and devices described herein allow a maximum number of fibers to be fit into the cartridge for use in administration of humidified breathing gas therapies. For example, the vapor transfer cartridge is manufactured in at least three discrete pieces, allowing the center tube to be extruded with a constant inner diameter that can accept more fibers. Manufacture of a cartridge in three pieces allows creation of a cartridge with a constant and maximized inner cross-sectional area such that a maximum number of fibers can be inserted into the cartridge without a minimum inner diameter limiting the number of fibers. The maximized number of fibers allows the cartridge to efficiently humidify the gas by providing ample surface area and consistent wetting of the fibers.

Additionally or alternatively, the systems, methods, and devices can be precisely assembled to fit existing systems. Vapor transfer cartridges are often fitted to a specific system, requiring the vapor transfer cartridge to be manufactured with certain dimensions. For example, the vapor transfer cartridges can be used in existing capital units that require a specific shape and size because the three-piece manufacturing allows for adjustments to precisely align and size the pieces. The extruded center tube may be manufactured with less strict tolerances, as the assembly of the center tube into channels on the header pieces allows the center tube to "float" within the channel and to be bonded at a position to attain the desired length. The alignment of ports on the vapor transfer cartridge is accomplished by fixturing during assembly to precisely align the ports. In some cases, the vapor transfer cartridge may be designed to be held by a patient or placed proximal to the patient (a "patient proximate" device). Such cases also require the vapor transfer cartridge to have certain dimensions for patient comfort in holding the device or having the device near to the patient.

Additionally, low-profile baffles at the ports prevent inconsistent wetting of the fibers and disperse the water throughout the cartridge while not limiting the number of fibers that can fit into the cartridge. Low profile baffles prevent snagging of fibers on the baffle during assembly of the vapor transfer cartridge. The baffles direct the flow of fluid throughout the cartridge and prevent the high pressure water from directly impacting the fibers as it enters the cartridge.

These systems, methods, and devices allow for a maximum inner diameter to be achieved within a limited size cartridge to maximize the number of fibers that can fit into the cartridge. This leads to efficient humidification of breathing gas for HFT systems and an efficient use of space. Rather than increasing the size of the system, the methods of manufacturing vapor transfer cartridges having three or more pieces allow the available space to be maximized. Low-profile baffles on fluid inlet and outlet ports further maximize the space available for fibers and protect the fibers from the fluid flow while providing consistent wetting of the fibers for humidification of the breathing gas.

FIG. 1 shows an illustrative respiratory therapy system 101 including vapor transfer cartridge 100, capital unit 103, and cannula 155 for delivery of humidified gas to patient. Capital unit 103 includes blower 161, heater 163, pump 165, and gas supply 167. Capital unit 103 includes gas outlet 145, gas inlet 147, fluid outlet 123, and fluid inlet 125. Vapor transfer cartridge 100 includes center tube 116, first header piece 118 including first port 122, first end cap 140 including third port 144, second header piece 120 including second port 124, and second end cap 142 including fourth port 146. Center tube 116 is coupled at first end 141 to first header piece 118. First header piece 118 is coupled to first end cap 140. Center tube 116 is coupled at second end 143 to second header piece 120. Second header piece 120 is further coupled to second end cap 142. Center tube 116 contains membranes, which may be configured as fibers (not shown) aligned along longitudinal axis 157 from first end 141 to second end 143.

Vapor transfer cartridge 100 is designed to interface with capital unit 103. As such, there are specific dimensions that must be met in order to allow successful coupling between vapor transfer cartridge 100, in particular water and gas ports, and capital unit 103, for example, by being inserted into a cavity 121. The capabilities of capital unit 103, such as accessible gas flow rate or fluid flow rates, may necessitate a change in the properties of vapor transfer cartridge 100. Because vapor transfer cartridge 100 must fit capital unit 103, the dimensions of vapor transfer cartridge 100 cannot be changed. However, other changes to vapor transfer cartridge 100, such as changes in a number or size of fiber in vapor transfer cartridge 100, may enable increased efficiency of respiratory therapy system 101 within the size constraints of the vapor transfer cartridge 100.

Manufacturing vapor transfer cartridge 100 from multiple components rather than tooling the vapor transfer cartridge 100 as a single unit allows center tube 116 to be manufactured by extrusion, rather than tooled with the headers attached, enabling inner diameter 134 of vapor transfer cartridge 100 to be maximized throughout center tube 116. Tooled vapor transfer cartridges have a minimum diameter at a center point of the center tube, because the diameter must increase to allow the tools to escape, limiting the number of fibers that can be inserted into the tube.

Blower 161 can be alternatively an air compressor or can be omitted in favor of a wall air source. Gas outlet 145 on capital unit 103 is coupled to third port 144 and provides gas to vapor transfer cartridge 100. Gas may be provided to vapor transfer cartridge 100 at a rate of eight liters per minute (LPM) or greater. Gas may be provided to vapor transfer cartridge 100 at a rate of 10 LPM, 12 LPM, 14 LPM or 16 LPM. The gas provided by gas supply 151 can be building gas or wall gas in a medical or hospital setting. Alternatively, the gas provided by gas supply 151 can be supplied by a canister or by an oxygen concentrator system. The gas travels through fibers within vapor transfer cartridge 100 and exits vapor transfer cartridge 100 at fourth port 146. Fourth port 146 is coupled to gas inlet 147. Fluid outlet 123 on capital unit 103 is coupled to first port 122 and provides fluid to vapor transfer cartridge 100. The fluid travels through vapor transfer cartridge 100 and exits vapor transfer cartridge 100 at second port 124. Second port 124 is coupled to fluid inlet 125 on capital unit 103.

In vapor transfer cartridge 100, heated fluid interacts with gas through a membrane (not shown), heating and humidifying the gas. Fluid and humidified gas enter capital unit 103 from vapor transfer cartridge 100 at gas inlet 147 and fluid inlet 125. The humidified gas exits capital unit 103 at breathing gas outlet 151. Humidified gas is transported through gas tube 153 consisting of medical grade tubing from capital unit 103 to cannula 155, where it is administered to the patient.

The membrane may consist of a plurality of hollow fibers arranged in vapor transfer cartridge 100. The membrane may be porous or non-porous. The constant inner diameter 134 of vapor transfer cartridge 100 allows a maximum number of fibers to be inserted into the available space in vapor transfer cartridge 100 for efficient and consistent wetting of the surface areas of the fibers with the heated fluid, resulting in efficient humidification of the gas inside the fibers. By maximizing inner diameter 134 of vapor transfer cartridge 100 through manufacture in multiple pieces, the number of fibers that fit in center tube 116 is maximized. This allows efficient humidification of gas given a space constraint, such as the constraint that vapor transfer cartridge 100 must fit into a cavity 121 of capital unit 103. In some implementations, vapor transfer cartridge 100 does not couple directly to capital unit 103, and instead is handheld by a patient or placed proximal to the patient, such as strapped to a bed railing. In such cases, vapor transfer cartridge 100 is manufactured to maintain certain dimensions for patient comfort. In some implementations, a length of vapor transfer cartridge 100 can be adjusted by varying a length of center tube 116 in order to comfortably fit the hand of a patient. For example, a shorter vapor transfer cartridge 100 can be manufactured for a pediatric patient, and a larger vapor transfer cartridge can be manufactured to fit an adult patient. In some implementations, center tube 116 is extruded such that a length of center tube 116 can be adjusted to provide larger vapor transfer cartridges 100 for faster humidification, or to fit a variety of capital units 103.

Manufacturing vapor transfer cartridge 100 from multiple components allows the ports to be precisely aligned to engage with outlets, inlets, or valves on capital unit 103. First port 122, second port 124, third port 144, and fourth port 146 are aligned along longitudinal axis 157 on a side of vapor transfer cartridge 100, but alternatively the ports can be arranged on vapor transfer cartridge 100 to accommodate other capital units 103 or systems. For example, in some implementations, the ports are positioned at either end of vapor transfer cartridge 100 to allow an axial flow of fluid and gas through vapor transfer cartridge 100. In some implementations, third port 144 and fourth port 146 are positioned on either end of vapor transfer cartridge 100, for example, at an end of first end cap 140 and second end cap 142, while first port 122 and second port 124 are positioned on a side of vapor transfer cartridge 100. In some implementations, first port 122, second port 124, third port 144, and fourth port 146 are all positioned at an end of first end cap 140 and second end cap 142. Positioning the ports at an end of first end cap 140 and second end cap 142 may be beneficial for implementations in which vapor transfer cartridge 100 is held by a patient, as positioning the ports at the ends prevents kinking during handling and allows an easier grip of vapor transfer cartridge 100. In some implementations, the ports may be spaced or aligned according to an arrangement of ports or valves on a capital unit, allowing simple manufacture of multiple designs or styles of vapor transfer cartridges 100 to fit a variety of capital units 103.

On vapor transfer cartridge 100, first header piece 118 is identical to second header piece 120. Alternatively, in some implementations, first header piece 118 is different from second header piece 120 in a manner that differentiates one side from another so as to facilitate correct placement of vapor transfer cartridge 100 in capital unit 103. In some implementations, first header piece 118 includes first end cap 140 and second header piece 120 includes second end cap 142, rather than the header pieces and end caps being manufactured separately. In some implementations, center tube 116 is manufactured with first header piece 118 attached, and second header piece 120 is added following insertion of fibers. In some implementations, the top of one or both of first end cap 140 and second end cap 142 is domed. In some implementations, the top of one or both of first end cap 140 and second end cap 142 is flat. The shape of the top of the end caps may differentiate one side from another to facilitate positioning of vapor transfer cartridge 100 in capital unit 103. In some implementations, a sensor (not shown) is disposed on vapor transfer cartridge 100 or capital unit 103, which senses that vapor transfer cartridge 100 is properly positioned in capital unit 103.

Vapor transfer cartridge 100 can be detached from capital unit 103 and is configured to be disposable. Disposable vapor transfer cartridge 100 allows the capital unit 103 to be used repeatedly with one or multiple patients while allowing vapor transfer cartridge 100 containing fibers with membranes to be replaced. While non-porous membranes are resistant to the ingress of bacteria, the constant flow of fluid through vapor transfer cartridge 100 necessitates regular replacement of vapor transfer cartridge 100. In order to be easily interchangeable, vapor transfer cartridge 100 includes precisely spaced inflow and outflow ports that connect to capital unit 103. The manufacturing of vapor transfer cartridge 100 must result in vapor transfer cartridge 100 of a specific length 135, having aligned ports that are precisely spaced.

Figure 2:
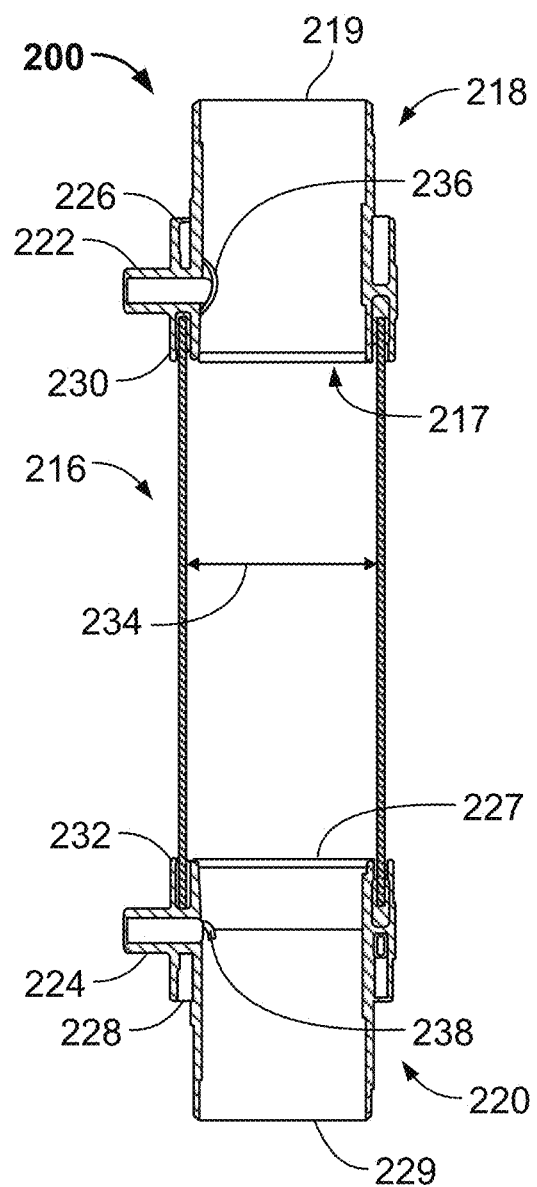
FIG. 2 shows an illustrative vapor transfer cartridge having three pieces and a constant inner diameter.

FIG. 2 shows an illustrative vapor transfer cartridge 200, including center tube 216, first header piece 218, and second header piece 220. As opposed to previous vapor transfer cartridges that were molded as a single unit, center tube 216, first header piece 218 and second header piece 220 are formed separately. Forming the components separately allows center tube 216 to be extruded rather than molded, resulting in lower costs and allowing a constant inner diameter. Vapor transfer cartridges molded as a single unit have a minimum diameter at the center of the center tube so that the tools do not become stuck. However, in molded single-piece vapor transfer cartridges, this minimum diameter is a limiting factor in determining the number of fibers that can fit into the vapor transfer cartridge. Forming center tube 216, first header piece 218, and second header piece 220 separately provides constant inner diameter 234 into which a maximum number of fibers can be fit. Center tube 216 is formed as a hollow tube with a constant inner diameter 234. By configuring center tube 216 as a hollow tube with constant inner diameter, the space in which fibers can be inserted is maximized. First header piece 218 includes first header end 217, second header end 219, first channel 230, first port 222, and first end cap slot 226. First header piece 218 is configured as a hollow tube between first header end 217 and second header end 219. Configuring first header piece 218 as a hollow tube allows fibers to be inserted into vapor transfer cartridge 200 through first header piece 218. First channel 230 is disposed about a circumference of first header piece 218 at first header end 217. First port 222 is disposed proximal to first header end 217 and provides an inlet with a nozzle extending radially outward from a center of first header piece. First baffle 236 is disposed inside vapor transfer cartridge 200 at first port 222. First end cap slot 226 is disposed near first port 222 as a channel or pocket about the exterior of first header piece 218 oriented toward second header end 219 of first header piece 218. First channel 230 is configured to accept an end of center tube 216 to couple first header piece 218 to center tube 216. By positioning first channel 230 on first header piece 218, the connection of center tube 216 and first header piece 218 has higher tolerances. Second header piece 220 includes third header end 227, fourth header end 229, second channel 232, second port 224, and second end cap slot 228. Like first header piece 218, second header piece 220 is configured as a hollow tube between third header end 227 and fourth header end 229. Second channel 232 is disposed about a circumference of second header piece 220 at third header end 227. Second port 224 is disposed proximal to third header end 227 and provides an outlet with a nozzle extending radially outward from a center of first header piece. Second baffle 238 is disposed inside vapor transfer cartridge 200 at second port 224. Second end cap slot 228 is disposed near second port 224 as a channel or pocket about the exterior of second header piece 220 oriented toward fourth header end 229 of second header piece 220. Second channel 232 is configured to accept an end of center tube 216 to couple second header piece 220 to center tube 216. First end cap slot 226 and second end cap slot 228 is configured to accept end caps (not shown) that include additional ports for the inflow and outflow of breathing gas.

Center tube 216, first header piece 218, and second header piece 220 are manufactured as three separate components that are then assembled to form vapor transfer cartridge 200. Forming these pieces in three separate units allows vapor transfer cartridge 200 to be constructed to specific dimensions while maximizing the space in which fibers can be inserted to guarantee efficient humidification of gas. Center tube 216 may be formed by extrusion or molding. First header piece 218 and second header piece 220 may be molded. By manufacturing center tube 216, first header piece 218, and second header piece 220 separately, inner diameter 234 of center tube 216 is not constricted at a center point and the number of fibers that can fit in the available cross-sectional area of center tube 216 is maximized. The constant inner diameter 234 of center tube 216 can be about 28 mm. In some implementations, constant inner diameter 234 is about 25 mm, 26 mm, 27 mm, 28 mm, 29 mm, 30 mm, 35 mm, 40 mm or any other suitable inner diameter. In some implementations, an extruded center tube 216 has a minimum inner diameter that is up to 50% larger than a molded center tube having the same external dimensions.

Figure 3:
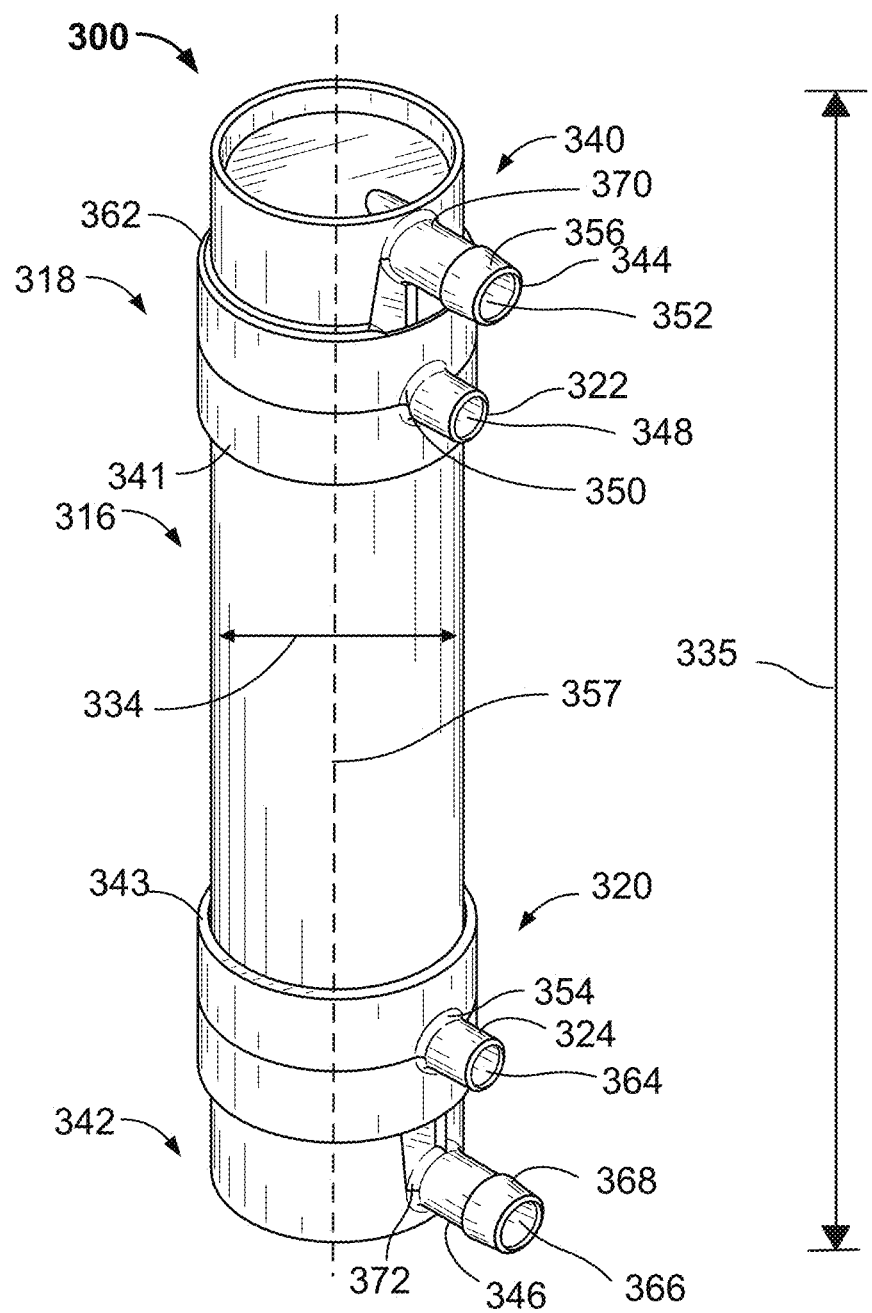
FIG. 3 shows an illustrative vapor transfer cartridge having three pieces with end caps.

While FIG. 2 shows a vapor transfer cartridge without end caps, FIG. 3 shows an illustrative vapor transfer cartridge 300 having end caps attached. Vapor transfer cartridge 300 includes center tube 316, first header piece 318 including first port 322, second header piece 320 including second port 324, first end cap 340 including third port 344, and second end cap 342 including fourth port 346. Center tube 316 is configured as a hollow tube with first end 341 and second end 343 and with a constant inner diameter 334. Center tube 316 is coupled to first header piece 318 at first end 341, and to second header piece 320 at second end 343. First header piece 318 is coupled to first end cap 340 at the end opposite the coupling with center tube 316. Second header piece 320 is coupled to second end cap 342 opposite the coupling with center tube 316. First port 322 includes first inlet 348 and first strengthening junction 350. Second port 324 includes first outlet 364 and second strengthening junction 354. Third port 344 includes first inlet 352, third strengthening junction 370, and first barb 356. Fourth port 346 includes second outlet 366, fourth strengthening junction 372, and second barb 368. Strengthening junctions 350, 354, 370 and 372 are added to a base of first port 322, second port 324, third port 344, and fourth port 346 to stabilize the coupling of the port with the header, in particular during insertion into and removal from the capital unit couplings. By adding strengthening junctions 350, 354, 370, and 372, the ports are stronger and less likely to break off when being attached to a capital unit or when being handled. In implementations in which the vapor transfer cartridge 300 is a patient proximate or handheld unit, such strengthening junctions enable vapor transfer cartridge 300 to withstand additional jostling or pressures that may occur in use. First barb 356 and second barb 368 allow vapor transfer cartridge 300 to securely couple to capital unit (e.g., capital unit 103 in FIG. 1) by engaging with gaskets at inlets and outlets of capital unit.

First port 322, second port 324, third port 344, and fourth port 346 are aligned along longitudinal axis 357 of vapor transfer cartridge 300. The alignment of first port 322, second port 324, third port 344, and fourth port 346 allows vapor transfer cartridge to easily couple and decouple from the inlets and outlets on the capital unit. Furthermore, length 335 of vapor transfer cartridge 300 can be adjusted during assembly of center tube 316, first header piece 318, and second header piece 320 such that length 335 is consistent across multiple vapor transfer cartridges 300. In this way, vapor transfer cartridge 300 is made to be used disposably or interchangeably with a capital unit.

Figure 4:
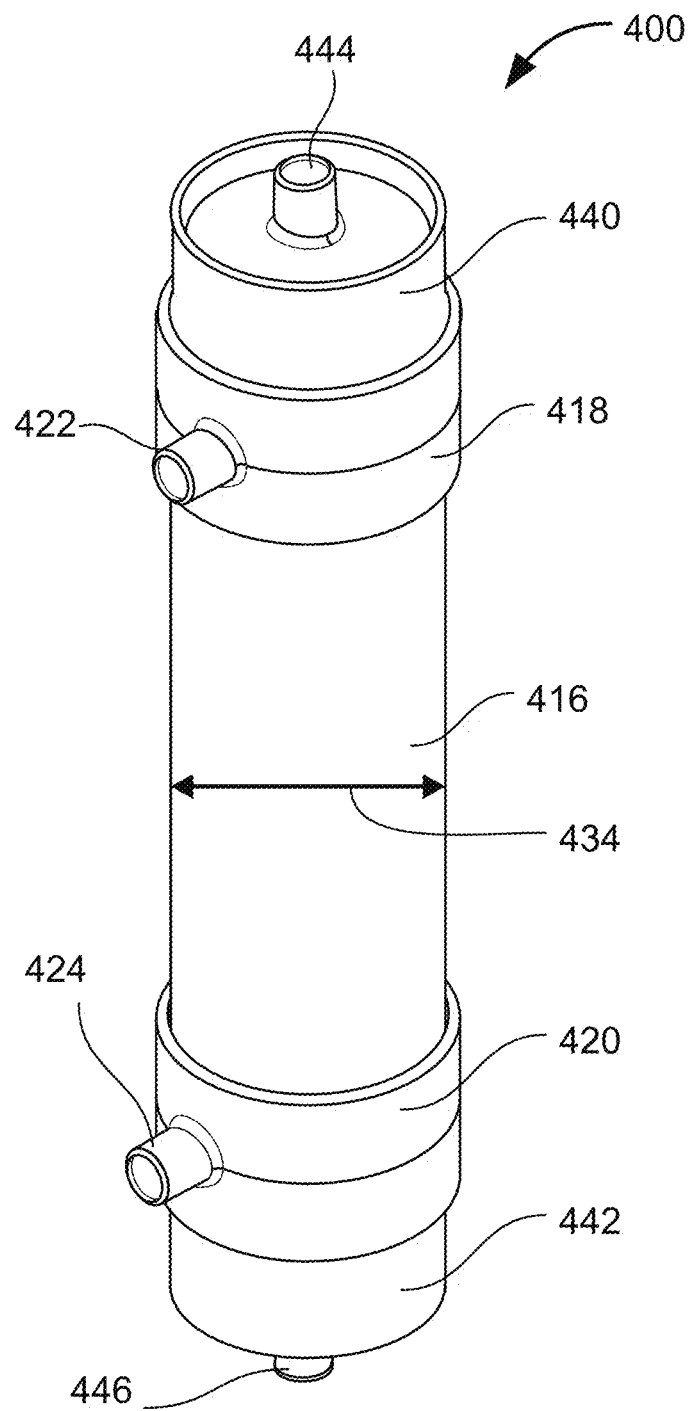
FIG. 4 shows an illustrative vapor transfer cartridge in which the ports are located either end of the vapor transfer cartridge.

While FIG. 3 shows an illustrative vapor transfer cartridge having ports aligned along a side of the vapor transfer cartridge, FIG. 4 shows an illustrative vapor transfer cartridge 400 in which the two gas ports are positioned at opposite ends of the vapor transfer cartridge 400. Ports may be positioned at an end of vapor transfer cartridge 400 to better fit an existing capital unit system or to provide a comfortable and safe fit for a handheld or patient proximate device. Vapor transfer cartridge 400 includes center tube 416, first header piece 418, second header piece 420, first end cap 440, and second end cap 442. Third port 444 is disposed at the top end of first end cap 440 at the top of vapor transfer cartridge 400 and fourth port 446 is disposed at the top end of second end cap 442 at the bottom of vapor transfer cartridge 400. First port 422 and second port 424 are disposed on a side of first header piece 418 and second header piece 420, respectively.

In some implementations, first port 422 and second port 424 are also disposed at the ends of first end cap 440 and second end cap 442 with third port 444 and fourth port 446. Placing one or more of the ports on an end of vapor transfer cartridge 400 may take advantage of an axial flow pattern to provide one or both of gas and water to fibers in vapor transfer cartridge 400. Moving the ports from a side of vapor transfer cartridge 400 to an end may also enable more fibers to be fit into the space, as baffles are then placed at an end of vapor transfer cartridge 400 rather than at the sides. By moving ports and baffles from the side of vapor transfer cartridge 400 to the end, the inner diameter 434 of center tube 416 and vapor transfer cartridge 400 is maximized to fit the maximum number of fibers possible. Furthermore, removing the baffles to an end of vapor transfer cartridge 400 prevents fibers from snagging on the baffles during insertion into vapor transfer cartridge 400.

In some implementations, one or more passages (not shown) may be configured within first end cap 440 and/or first header piece 418 to direct the inflow from third port 444 from the end of first end cap 440 into the body of center tube 416. Similar passages may be configured within second end cap 442 and/or second header piece 420. In some implementations, first header piece 418 and first end cap 440 are configured as a single unit when third port 444 is positioned at an end of vapor transfer cartridge 400. In some implementations, first header piece 418 and first end cap 440 are configured as separate units and attached to vapor transfer cartridge 400 at different times during manufacture to allow fibers or potting material to be inserted into vapor transfer cartridge 400. In some implementations only one of third port 444 and fourth port 446 is positioned on an end of vapor transfer cartridge 400.

Figure 5:
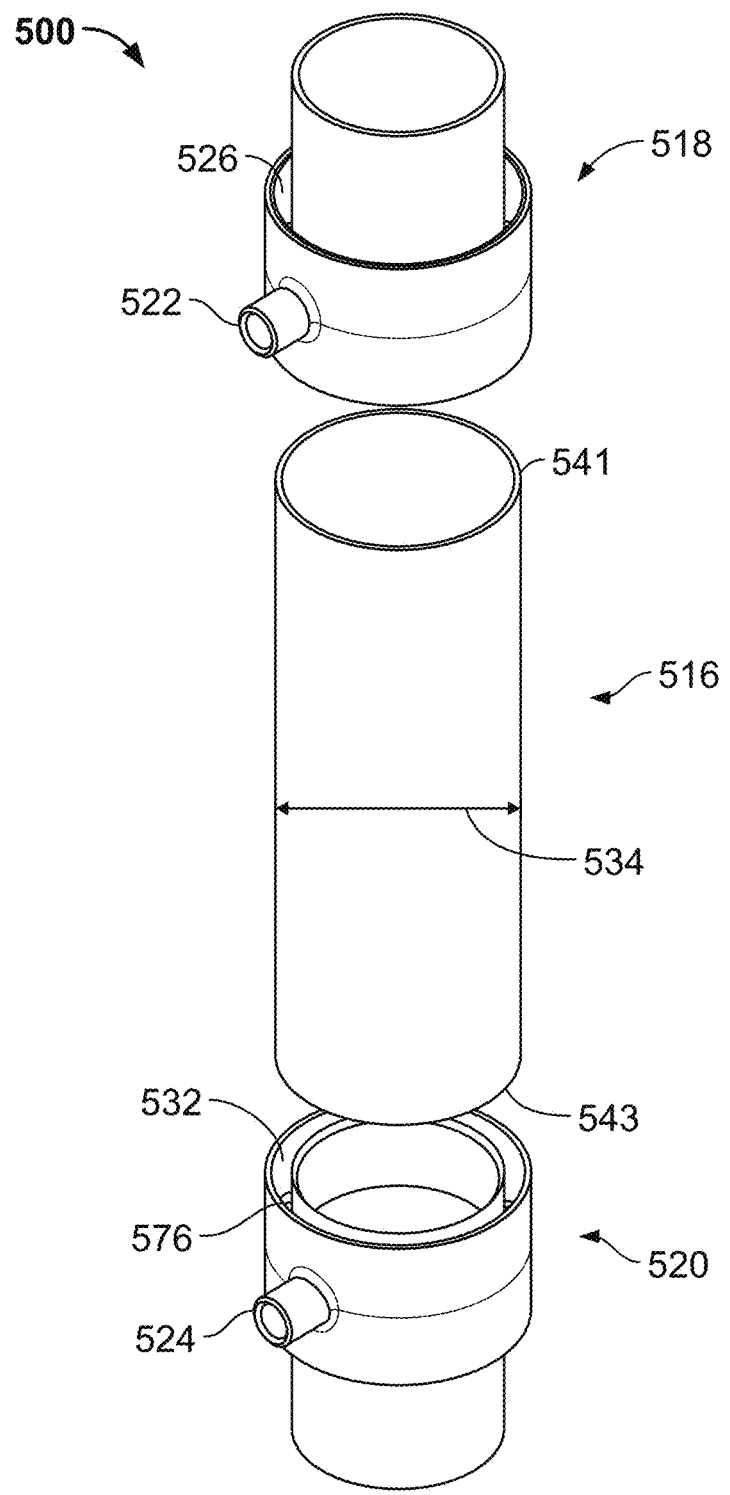
FIG. 5 shows an illustrative exploded view of a vapor transfer cartridge having three pieces.

FIG. 5 shows an illustrative exploded view of a vapor transfer cartridge 500, including center tube 516, first header piece 518, and second header piece 520. First header piece 518 includes first port 522 and first end cap slot 526 for coupling to an end cap (not shown). Second header piece 520 includes second port 524, second channel 532 and centering rib 576. Center tube 516 has first end 541 and second end 543. Center tube 516 has inner diameter 534, which is constant throughout the length of center tube 516. Vapor transfer cartridge 500 has its widest inner diameter 534 in center tube 516, and the inner diameter of vapor transfer cartridge 500 decreases at the coupling between center tube 516 and first header piece 518 and second header piece 520. The maximized inner diameter 534 in center tube 516 allows the number of fibers inserted into center tube 516 to be maximized.

The coupling of center tube 516 at second end 543 with second header piece 520 (and first header piece 518 at first end 541, not shown) allows the length of vapor transfer cartridge 500 to be adjusted by slight axial adjustment of center tube 516 within second channel 532. During coupling of center tube 516 with first and second header pieces 518 and 520, first end 541 of center tube 516 is inserted into the first channel (e.g., first channel 330 in FIG. 3) and is affixed within the first channel using polyurethane, or any similar suitable adhesive material. Holding first header piece 518 in position, second end 543 of center tube 516 is then inserted into second channel 532, which also contains polyurethane or another affixing or adhesive substance. Center tube 516 is stretched over centering rib 576, which centers center tube 516 and forms center tube 516 into a circular shape. Joining center tube 516 to first header piece 518 over centering rib 576 allows center tube 516 to be centered in the first channel so that vapor transfer cartridge 500 has precise shape and dimensions. Furthermore, centering ribs 576 prevent center tube 516 from shifting to one side within first channel. The first channel also contains centering ribs (not shown).

Second end 543 of center tube 516 can be inserted into second channel 532 such that second end 543 extends more or less into second channel 532, increasing or decreasing the overall length of vapor transfer cartridge 500 by increasing or decreasing the overlap between second end 543 of center tube 516 and second header piece 520. This adjustment of center tube 516 length allows the overall length of vapor transfer cartridge 500 to be controlled in order to fit into capital unit (e.g., capital unit 103 in FIG. 1). Center tube 516 may be allowed to "float" axially within second channel 532 in order to provide vapor transfer cartridge 500 of desired length. Floating center tube 516 during assembly allows center tube to have less strict tolerances, as minor variations in tube length can be accounted for by the association of center tube 516 within the first channel. In some implementations, +/−1 mm of tolerance is allowed in the length of center tube 516, which can be accommodated by adjusting an amount of second end 543 that extends into second header piece 520. Second end 543 of center tube 516 can be inserted into second channel 532 an amount that attains the desired overall vapor transfer cartridge 500 length. During assembly of vapor transfer cartridge 500, first header piece 518 and center tube 516 may be held, while second header piece 520 is brought into position on second end 543 of center tube 516 to attain the desired overall vapor transfer cartridge 500 length. The adjustable length of center tube 516 further allows center tube 516 to be extruded with less strict tolerances in length.

First port 522 and second port 524 are aligned during coupling of center tube 516 with first header piece 518 and second header piece 520. First port 522 and second port 524 may be aligned by fixturing during assembly. Fixturing first port 522 and second port 524 ensure that the ports on first header piece 518 and second header piece 520 are aligned. Furthermore, fixturing during assembly assures that first port 522 and second port 524 are located precisely relative to one another. In some implementations, the ports are not aligned along a longitudinal line, but may be positioned on vapor transfer cartridge 500 in any suitable order to fit an existing capital unit. Manufacturing vapor transfer cartridge 500 in multiple pieces allows the ports to be positioned in a variety of orientations in order to fit a variety of capital units.

Figure 6:
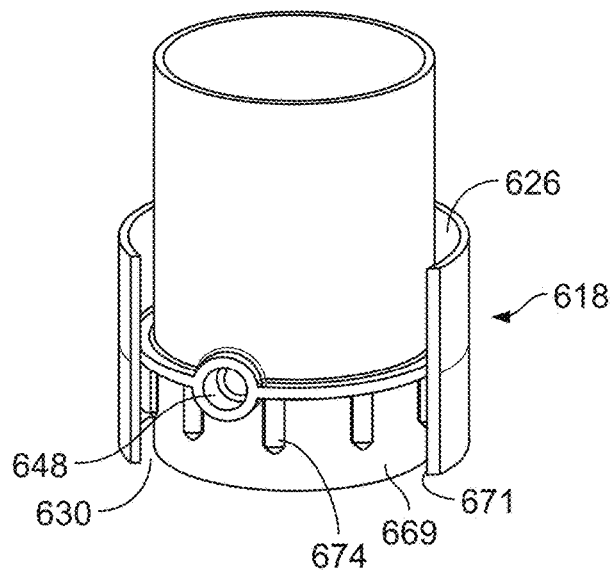
FIG. 6 shows an illustrative view of a header piece in a vapor transfer cartridge having three pieces.

FIG. 6 shows an illustrative view of a first header piece 618, including centering ribs 674. First header piece 618 includes first end cap slot 626, first channel 630, centering ribs 674, and first inlet 648. Centering ribs 674 extend within first channel 630 from first surface 669 of first channel 630. Centering ribs 674 can extend about 0.5 mm into first channel 630 from first surface 669. Centering ribs 674 may be spaced about the circumference of first channel 630. Including centering ribs 674 in first channel 630 allows the center tube to be centered on the first header piece 618 during assembly, rather than to one side or another as might occur without centering ribs 674. Precise centering allows a vapor transfer cartridge to be precisely dimensioned and shaped in order to fit into an existing capital unit. Centering ribs 674 on first surface 669 of first channel 630 allows the center tube (not shown) to slide over centering ribs 674, centering and shaping center tube 616 while also allowing the center tube to be inserted into first channel 630 an amount that attains the appropriate overall length of the vapor transfer cartridge. In some implementations, there are three centering ribs 674. In some implementations, there are three, four, six, eight, 10, 12, 16 or any suitable number of centering ribs 674 spaced on first surface 669 about a circumference of first channel 630. In some implementations, centering ribs 674 do not contact second surface 671 of first channel 630. Centering ribs 674 allow the length of the center tube to be adjusted in order to produce vapor transfer cartridges of varying lengths, or to allow less strict tolerances to be observed during production of center tubes while still achieving a precise length of vapor transfer cartridge to fit with an existing system.

Figure 7:
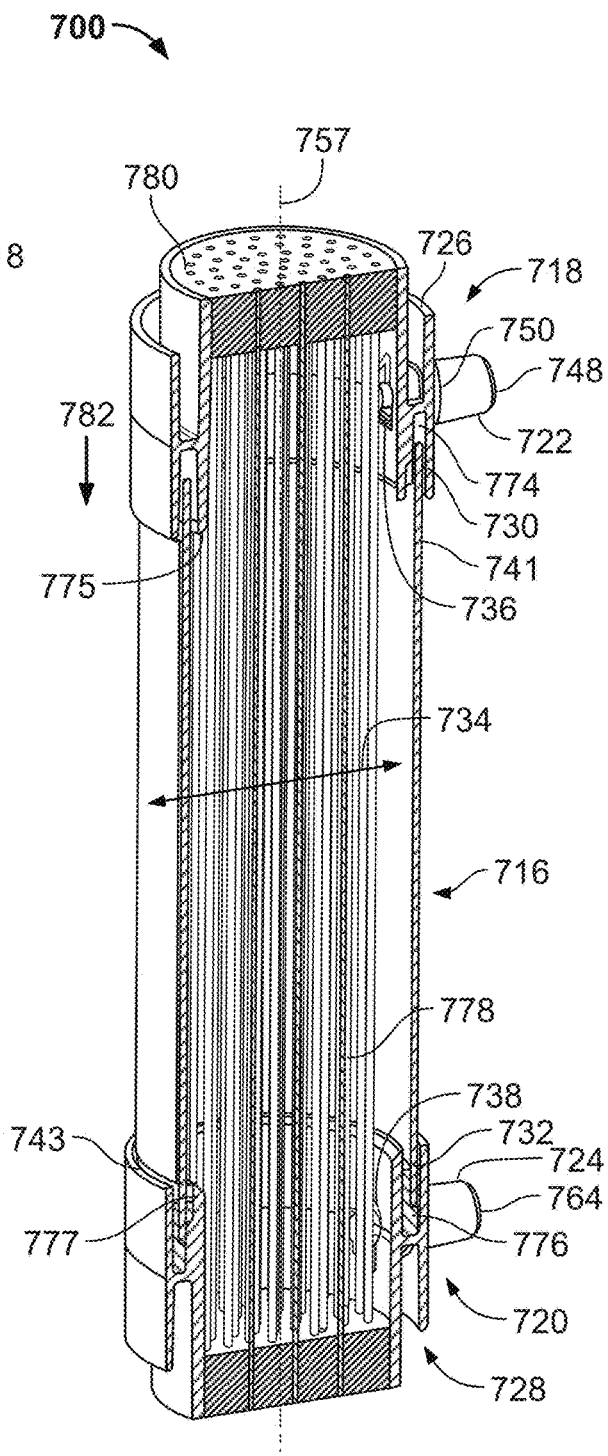
FIG. 7 shows an illustrative cross-sectional view of a vapor transfer cartridge having three pieces.

FIG. 7 shows an illustrative cross-sectional view of vapor transfer cartridge 700, including center tube 716, first header piece 718, second header piece 720, and fibers 778. First header piece 718 includes first channel 730, first centering rib 774, first port 722, and first end cap slot 726. Second header piece 720 includes second channel 732, second centering rib 776, second port 724, and second end cap slot 728. First port 722 includes first strengthening junction 750 and first inlet 748. First port 722 also includes first baffle 736 inside first header piece 718 at first inlet 748. First baffle 736 serves to disperse fluid entering vapor transfer cartridge 700 at first inlet 748. Second port 724 includes first outlet 764 and second baffle 738. Second baffle 738 forces the fluid to enter first outlet 764 from multiple directions and prevents fibers 778 from being sucked out first outlet 764. Second baffle 738 may also allow vapor transfer cartridge 700 to be coupled to a capital unit reversibly, that is, with second port 724 serving as an inlet rather than an outlet. Allowing vapor transfer cartridge 700 to be coupled to a capital unit in multiple orientations may increase the ease of use of vapor transfer cartridge 700.

First header piece 718 includes first edge slope 775 at an inner edge of first channel 730. First edge slope 775 centers fibers 778 as they are inserted into vapor transfer cartridge 700. Additionally, first edge slope 775 slopes toward a wall of center tube 716 such that, during insertion of fibers 778, fibers 778 do not become caught in first channel 730. Instead, fibers 778 are guided into first header piece 518 by edge slope 775. Second header piece 720 may also include second edge slope 777. First edge slope 775 and second edge slope 777 may have a slope of about 45°. Alternatively, first edge slope 775 and second edge slope 777 may have slopes of 25°, 30°, 45°, 50°, 60°, or any other suitable slope. During assembly of vapor transfer cartridge 700, fibers 778 are inserted into center tube 716 before one or both of first header piece 718 and second header piece 720 are coupled to center tube 716. First edge slope 775 and second edge slope 777 may guide fibers into the headers during placement of first header piece 718 and second header piece 720 onto center tube 716.

Fibers 778 are held in place within vapor transfer cartridge 700 by potting material 780, which allows gas to enter fibers 778 at their open ends and move through fibers 778 in direction 782. Fluid enters vapor transfer cartridge 700 at first inlet 748 in first port 722 and is dispersed in multiple directions by first baffle. The fluid contacts the exterior of fibers 778, interacts with fibers 778, and the fluid humidifies the gas passing through fibers 778. The gas continues through fibers 778 and exits vapor transfer cartridge 700.

Fibers 778 are positioned within center tube 716 aligned along longitudinal axis 557 from first end 741 of center tube 716 to second end 743 of center tube 716. Fibers 778 are inserted into vapor transfer cartridge 700 in an amount to fill the available space dictated by inner diameter 734 of center tube 716. Filling the available space with fibers 778 leads to efficient humidification of gas within the fibers as more fibers 778 of a given diameter results in more fiber surface area through which heated water can humidify gas. Fibers 778 can be about 0.7 mm in diameter. Alternatively, fibers 778 can have a diameter of about 0.3 mm, 0.5 mm, 0.7 mm, 0.9 mm, or any other suitable diameter. Up to 20, 50, 100, 1000, or any other suitable number of fibers 778 can be inserted into vapor transfer cartridge 700. In some implementations, a number of fibers 778 are inserted into vapor transfer cartridge 700 such that fibers 778 have a hexagonally close-packed structure. In some implementations, fibers 778 are inserted into vapor transfer cartridge 700 such that fibers 778 occupy about 50% of a cross-sectional area of center tube 716. Alternatively, in some implementations, fibers 778 are inserted into vapor transfer cartridge 700 such that fibers 778 occupy about 45%, 50%, 60%, 75% or any suitable percent of a cross-sectional area of center tube 716.

Figure 8:
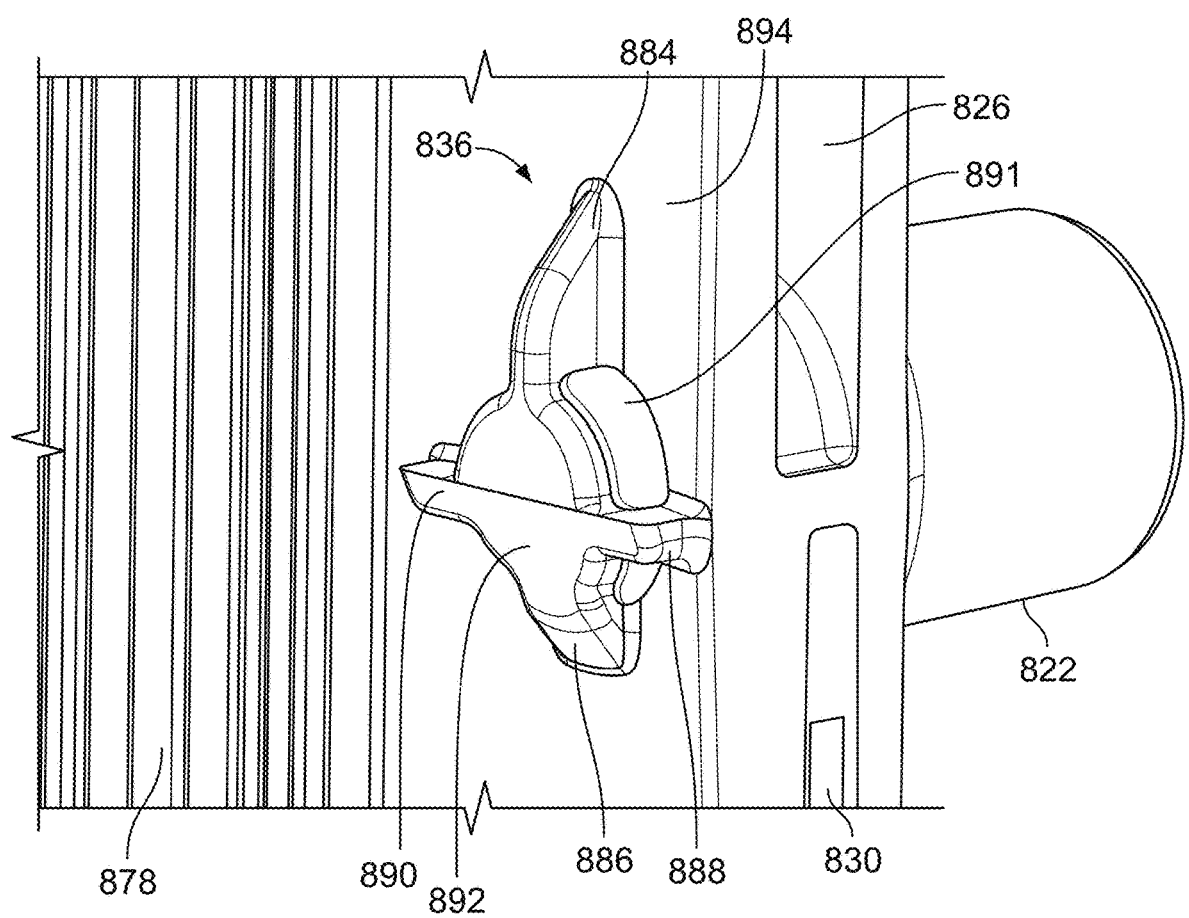
FIG. 8 shows an illustrative view of an omnidirectional baffle.

FIG. 8 shows an illustrative view of an omnidirectional baffle 836 at the inside of first port 822 of a vapor transfer cartridge. Omnidirectional baffle 836 consistently spreads water throughout the interior of vapor transfer cartridge without damaging fibers 878 near baffle 836. Baffle 836 includes outer longitudinal baffle support 884, inner longitudinal baffle support 886, first lateral baffle support 888, second lateral baffle support 890, and dispersing cap 892. Outer longitudinal baffle support 884, inner longitudinal baffle support 886, first lateral baffle support 888, and second lateral baffle support 890 are positioned in an a cross-like configuration, with each of outer longitudinal baffle support 884, inner longitudinal baffle support 886, first lateral baffle support 888, and second lateral baffle support 890 extending from interior surface 894 toward an interior of first header piece. Outer longitudinal baffle support 884, inner longitudinal baffle support 886, first lateral baffle support 888, and second lateral baffle support 890 meet dispersing cap 892 above an baffle opening 891 in fluid connection to first port 822. Fluid may escape from baffle opening 891 through four holes in baffle 836 defined by interior surface 894 and outer longitudinal baffle support 884, inner longitudinal baffle support 886, first lateral baffle support 888, and second lateral baffle support 890. Due to the three piece design, baffle 836 may be tooled. For example, baffle 836 may be formed during tooling of first header piece. Baffle 836 extends only a short distance into an interior of vapor transfer cartridge so as not to decrease the space available for fibers 878. Baffle 836 can be formed without undercuts and is minimally invasive of the space available for fibers 878. Baffle 836 is configured so as not to encroach on the interior space of vapor transfer cartridge, and is further configured so as to prevent snagging of fibers 878 on baffle 836 during insertion into the vapor transfer cartridge. Baffle 836 can extend into first header piece a distance of about four mm or less. Alternatively, baffle 836 can extend into first header piece a distance of about one mm, two mm, four mm, five mm, 10 mm or any suitable distance. First end cap slot 826 and first channel 830 pass near first port 822.

Manufacturing an omnidirectional baffle 836 that does not encroach on the interior diameter of vapor transfer cartridge allows the inner diameter to be preserved for a maximum number of fibers 878. Baffle 836 extends into the center of vapor transfer cartridge by a small amount only, so that baffle 836 does not encroach on the space available in the center tube or first header piece. Additionally, baffle 836 is designed to prevent snagging of fibers 878 during insertion into vapor transfer cartridge. For example, inner longitudinal baffle support 886 is configured such that during insertion of fibers 878 into vapor transfer cartridge, fibers 878 encounter a smooth edge of inner longitudinal baffle support 886 and are guided around baffle 836 rather than snagging or being forced through baffle 836.

During use, fluid enters through first port 822 and travels to baffle opening 891. The fluid flow into a vapor transfer cartridge is a high velocity stream of water. High velocity fluid entering the vapor transfer cartridge and hitting fibers 878 directly can damage or break fibers 878. Fluid encounters dispersing cap 892 of baffle 836 and is directed into an omnidirectional flow having a near-360 degree radius of flow into the vapor transfer cartridge. Fluid moves out from baffle 836 and disperses throughout the vapor transfer cartridge along interior surface 894 of the vapor transfer cartridge before interacting with fibers 878. The relative size and position of outer longitudinal baffle support 884, inner longitudinal baffle support 886, first lateral baffle support 888, second lateral baffle support 890, and dispersing cap 892 can be altered in order to encourage flow in a particular direction, for example, toward the end of fibers 878.

The omnidirectional flow of baffle 836 encourages fluid flow throughout vapor transfer cartridge leading to efficient and consistent wetting of fibers 878. Furthermore, the positioning of dispersing cap 892 and the resulting omnidirectional flow along interior surface 894 of first header piece 818 keeps the fluid from being directed predominately at a few fibers 878 near first port 822. Fibers 878 are delicate and can break or extend when subjected to high fluid forces, as from a direct jet of water through first port 822. Baffle 836 protects fibers 878 from the impact of the fluid flow and distributes the fluid over fibers 878 throughout vapor transfer cartridge.

Baffle 836 can also be used at an outlet port. An outlet port of a vapor transfer cartridge could become blocked by a single fiber or a group of fibers 878 if they are pulled into the outlet by the flow of fluid. Baffle 836, including outer longitudinal baffle support 884, inner longitudinal baffle support 886, first lateral baffle support 888, second lateral baffle support 890, and dispersing cap 892, covers the outlet port and prevents the outlet from becoming blocked.

In some implementations, a baffle may have more or less baffle supports than depicted. For example, baffle 836 may have three baffle supports resulting in three holes in baffle 836 rather than four through which water enters the vapor transfer cartridge. Baffle 836 may be configured to have two, three, four, five, six, eight, 12, or any suitable number of baffle supports. In some implementations, baffle supports are equally spaced. Baffle supports can be configured to prevent snagging of fibers on baffle 836. Dispersing cap 892 may be shaped as a circle. Alternatively, dispersing cap 892 may be shaped as an oval, a square, a triangle, or any suitable shape. The shape of dispersing cap 892 is configured to facilitate the spread of fluid in certain directions.

Baffle 836 can be manufactured from various materials, including a variety of plastics and polymers. In some implementations, baffle 836 is tooled during manufacture of first header piece. In some implementations, baffle 836 is located in a side of the center tube or a side or end of first end cap. In some implementations, baffle 836 is molded. In some implementations, baffle 836 is injection-molded. In some implementations, baffle 836 is added to first header piece after manufacture. In some implementations, baffle 836 is partially formed during manufacture of first header piece and is later completed. In some implementations, baffle 836 is partially formed and is plastically deformed into a final shape or position.

Figure 9:
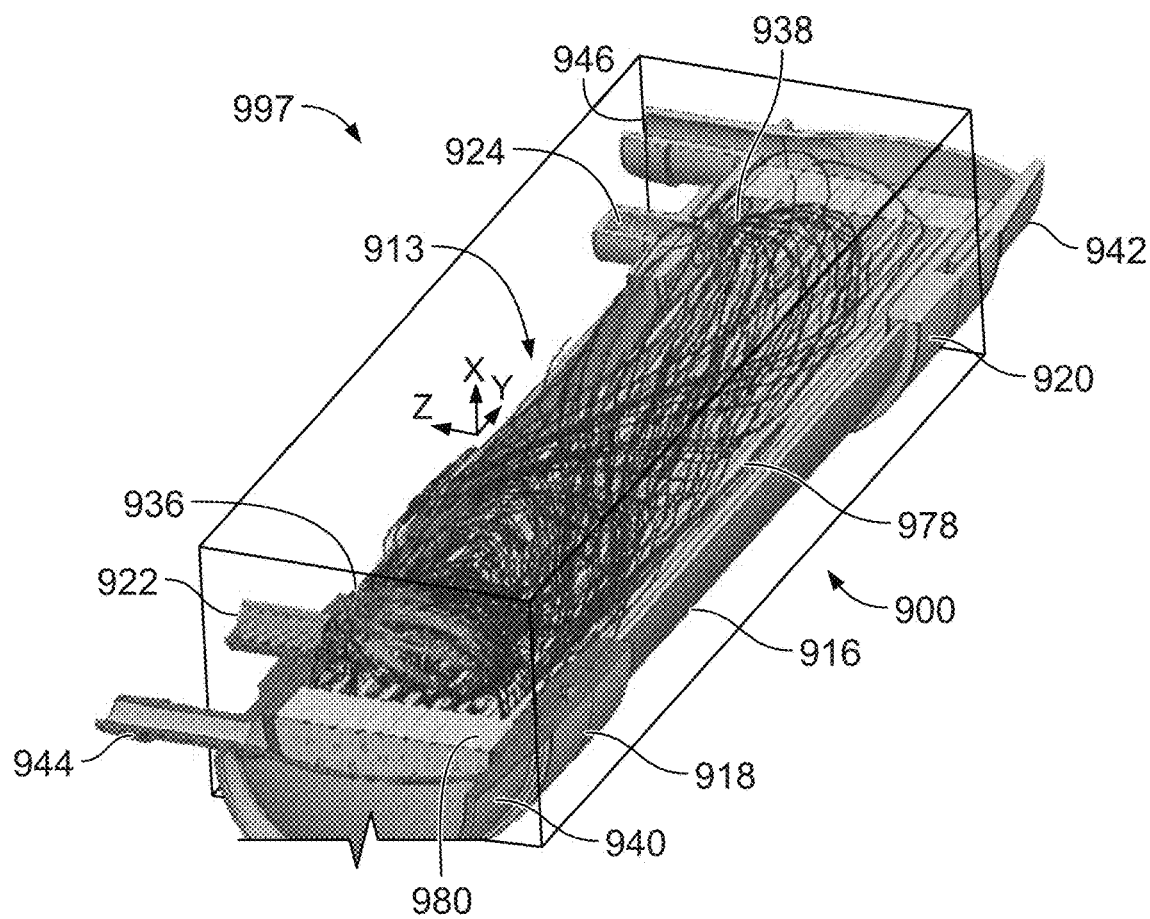
FIG. 9 shows an illustrative view of flow pattern from the omnidirectional baffle of FIG. 6 within a vapor transfer cartridge.

FIG. 9 shows an illustrative view of the flow pattern from the omnidirectional baffle 836 of FIG. 8 within a vapor transfer cartridge 900 determined by computations fluid dynamics (CFD) analysis. Vapor transfer cartridge 900 in plot 997 includes center tube 916, fibers 978, first header piece 918, first end cap 940, second header piece 920, second end cap 942, first baffle 936, and second baffle 938. Gas flows through vapor transfer cartridge 900 beginning at third port 944 in first end cap 940, through fibers 978 held in place by potting material 980, through center tube 916 within fibers 978, and out fourth port 946 in second end cap 942. Fluid flows through vapor transfer cartridge 900 beginning at first port 922 in first header piece 918 where it encounters first baffle 936. Fluid is dispersed by first baffle 936 and flows around the interior of center tube 916 where fluid interacts with fibers 978, humidifying the gas within fibers 978. Fluid ends at second port 924 in second header piece 920, wherein the fluid enters second port 924 by going through second baffle 938.

Plot 997 includes flow pattern 913 showing the flow of fluid into vapor transfer cartridge 900 through first port 922 with a uniform flow velocity and without formation of channels. A consistent movement of water throughout the entirety of vapor transfer cartridge 900 ensures that all fibers are wetted and efficient humidification can occur. Plot 997 shows flow pattern 913 dispersing from first port 922 due to first baffle 936 and moving about fibers 978 and throughout vapor transfer cartridge 900. Flow pattern 913 shows fluid exiting vapor transfer cartridge 900 at second port 924. Flow pattern 913 demonstrates efficient wetting of fibers 978 along the length of vapor transfer cartridge 900. Decreased flow pattern 913 around fibers 978 near second port 924 is partially due to loss of fluid to humidification of the gas in fibers 978 throughout the length of vapor transfer cartridge 900.

Figure 10:
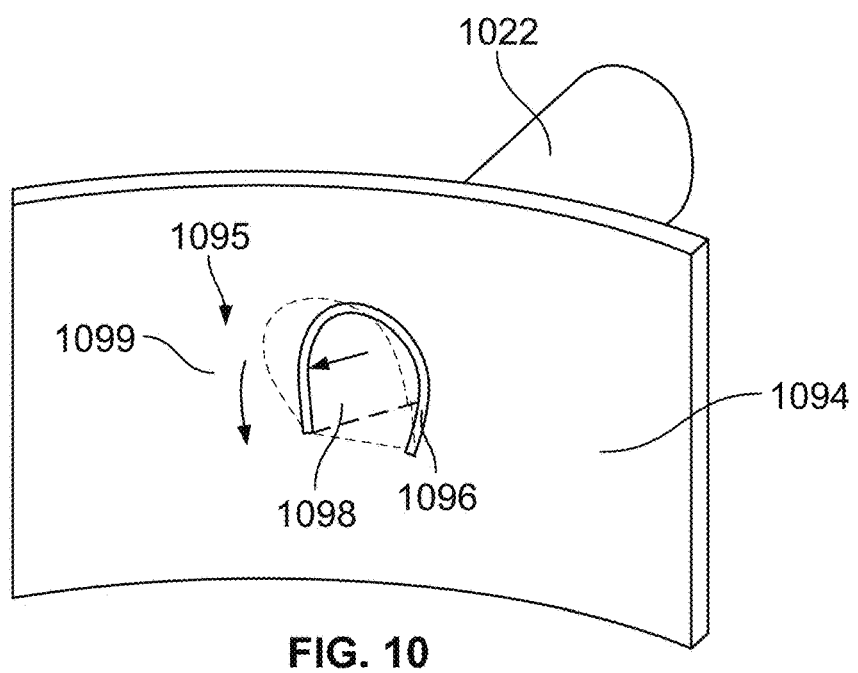
FIG. 10 shows an illustrative view of an alternative baffle design.

FIG. 10 shows an illustrative view of an alternative baffle 1095. Alternative baffle 1095 includes horseshoe puncture 1096 and horseshoe flap 1098. Alternative baffle 1095 can be configured as part of first header piece and extended into the center of vapor transfer cartridge after fibers have been inserted, preventing snagging of fibers on alternative baffle 1095. Alternative baffle 1095 is formed in interior wall 1094 of first header piece and can be flush with the wall during manufacture, increasing interior space available for the insertion of fibers. Alternative baffle 1095 can be tooled during the manufacture of the first header piece, or can be punched into interior wall 1094 of the first header piece after manufacture of the first header piece. Alternative baffle 1095 is positioned at inlet of first port 1022, where horseshoe puncture 1096 shaped as a partial puncture of interior wall 1094 is positioned during manufacture. Following manufacture of a vapor transfer cartridge (e.g., vapor transfer cartridge 100 in FIG. 1, 200 in FIG. 2, 300 in FIG. 3, 400 in FIG. 4, 500 in FIG. 5), and after fibers have been placed within the vapor transfer cartridge, horseshoe puncture 1096 may be pressed inward in direction 1099 toward a center of the vapor transfer cartridge, such that horseshoe flap 1098 extends into the vapor transfer cartridge. Horseshoe flap 1098 can be attached to the wall at a hinge-like coupling that allows horseshoe flap 1098 to remain attached to interior wall 1094 while it is bent into the interior of the vapor transfer cartridge. The coupling of horseshoe flap 1098 to interior wall 1094 where alternative baffle 1095 bends into the vapor transfer cartridge can be perforated or scored to facilitate bending.

Alternative baffle 1095 allows fibers (not shown) to be inserted into the vapor transfer cartridge without any decrease in space available for fibers due to a baffle extending from interior wall 1094 of first header piece. Fibers can be inserted using the full available space in the vapor transfer cartridge. After insertion of the fibers, alternative baffle 1095 may be pushed into the vapor transfer cartridge to allow fluid to enter. Alternative baffle 1095 does not protrude from interior wall 1094 of first header piece until it is pushed in direction 1099. Thus, fibers 1078 can be inserted without concern for snagging fibers 1078 on a protruding baffle during insertion. Alternative baffle 1095 disperses fluid in multiple directions along interior wall 1094 of first header piece. Alternative baffle 1095 can be oriented to direct fluid toward center tube (e.g., center tube 116 in FIG. 1). In some implementations, alternative baffle 1095 is oriented to direct fluid away from center tube.

Alternative baffle 1095 can also be used at an outlet port (not shown). Alternative baffle 1095 prevents fibers 1078 from being pulled into the outlet port where they could block the flow of fluid exiting vapor transfer cartridge.

Alternative baffle 1095 is located in a side of the first header piece. Alternatively, in some implementations, alternative baffle 1095 is located in a side of the first end cap. In some implementations, alternative baffle 1095 is located in an end of the first end cap. In some implementations, alternative baffle 1095 is located within the center tube. In some implementations, a baffle is formed in the center tube. In some implementations, a baffle is formed by aligning a port on the first header piece with a portion of the center tube, such that fluid entering through the port encounters an outer edge of the center tube and is directed upward and over the end of the center tube and into the body of the center tube. Using the center tube as a portion of the baffle may decrease the complexity of manufacture and further prevents snagging of fibers since there is no component extending into the center tube.

In some implementations, alternative baffle 1095 is manufactured during manufacture of first header piece. Alternatively, alternative baffle 1095 can be added to first header piece later. In some implementations, alternative baffle 1095 is stamped or cut into first header piece. In some implementations, alternative baffle 1095 is shaped as a triangle, circle, square, half-moon, or other suitable shape.

Figure 11:
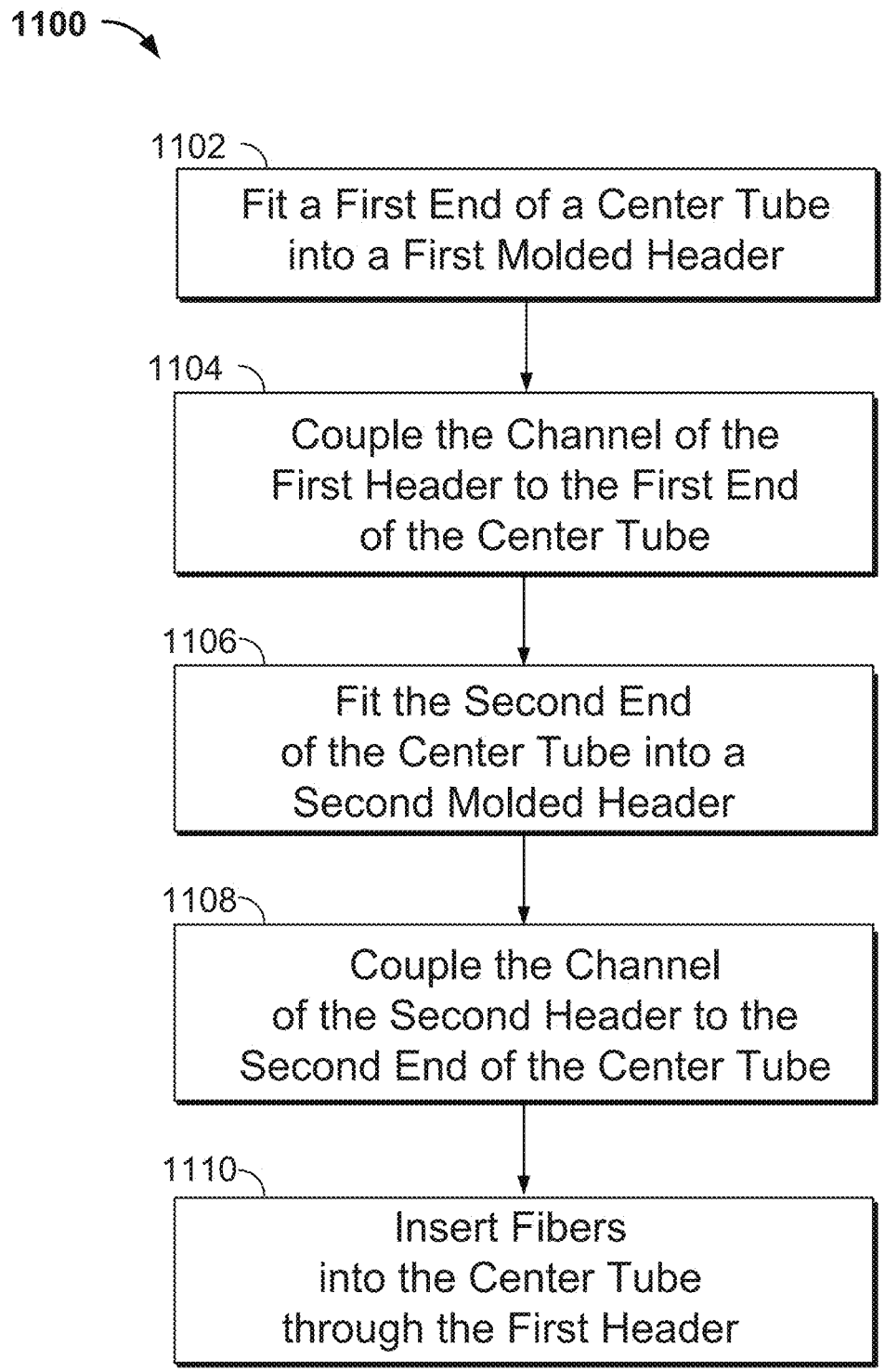
FIG. 11 shows a flow chart of a method of manufacturing a vapor transfer cartridge having three pieces.

FIG. 11 shows an illustrative process 1100 for manufacturing a vapor transfer cartridge. The process 1100 can be used to manufacture a vapor cartridge having a constant inner diameter, such as vapor transfer cartridge 100 in FIG. 1, 200 in FIG. 2, 300 in FIG. 3, 400 in FIG. 4, 500 in FIG. 5, 700 in FIG. 7, or any other suitable vapor transfer cartridge. In step 1102, a first end of center tube is fitted onto a first molded header. The center tube, such as center tube 116 in FIG. 1, 216 in FIG. 2, 316 in FIG. 3, 416 in FIG. 4, 516 in FIG. 716 in FIG. 7 or 816 in FIG. 8, is configured as a hollow tube, having a first end and a second end and a continuous inner diameter throughout. The continuous inner diameter can be about 28 mm. Alternatively, the continuous inner diameter can be about 25 mm, 26 mm, 27 mm, 28 mm, 29 mm, 30 mm, 35 mm, 40 mm or any other suitable inner diameter. The molded header, such as first header piece 118 in FIG. 1, 218 in FIG. 2, 318 in FIG. 3, 418 in FIG. 4, 518 in FIG. 718 in FIG. 7 or 818 in FIG. 8, is constructed as a cap sized to fit on and about an end of the center tube and having a channel about an inner circumference. The molded header has at least one port on a side of the header and a baffle configured at the port. In some implementations, the molded header may include both a header piece and the end cap, and therefore may include two or more ports.

In step 1104, the channel of the first header piece is coupled to the first end of the center tube. The header is coupled to the center tube using polyurethane or a similar adhesive product. Polyurethane is placed in the channel of the first header piece and the center tube is inserted into the polyurethane to bind the first header piece and center tube.

In step 1106, the second end of the center tube is fit into a second molded header. In step 1108, the channel of the second header piece is coupled to the center tube. This is accomplished by placing polyurethane in the channel of the second header piece. The center tube may be inserted into the channel of the second header piece a changeable amount in order to control the overall length of the vapor transfer cartridge. Additionally, one or more ports on the first header piece is aligned with one or more ports on the second header piece. In some implementations, a baffle is positioned at each of the ports.

In step 1110, fibers are placed into the center tube through the first header piece. Fibers are placed into the center tube in sufficient number to fill the center tube. Fibers are inserted in a bundle. In some implementations, fibers are inserted in a paper wrapping that is later removed. In some implementations, the fibers are 0.7 mm in diameter. In some implementations, the fibers have a diameter of 0.3 mm, 0.5 mm, 0.7 mm, 0.9 mm, or any other suitable diameter. In some implementations, about 250-700 fibers are inserted into the center tube. For example, 300, 400, 500, or 600 fibers may be inserted into the center tube. In some implementations, the fibers inserted into the center tube are so numerous that, viewed from an end, the fibers form a hexagonally close packed structure. In some implementations, fibers 778 are inserted into vapor transfer cartridge 700 such that fibers 778 occupy about 50% of a cross-sectional area of center tube 716. Alternatively, fibers 778 can be inserted into vapor transfer cartridge 700 such that fibers 778 occupy about 45%, 50%, 60%, 75% or any suitable percent of a cross-sectional area of center tube 716. In some implementations, up to 20, 50, 100, 1000, or any other suitable number of fibers are inserted into the center tube. In some implementations, fibers are inserted into the center tube before coupling one or both of the first header piece and the second header piece to center tube.

In some implementations, after placing the fibers in the center tube, the fibers are then held in position at the first header piece and the second header piece by potting material. Potting material may be injected into the first header piece and the second header piece during or before centrifugation. After injection, the centrifugation of the vapor transfer cartridge distributes the potting material at the first header piece and the second header piece where it serves to bond the ends of the fibers together to hold them in place. The potting material may be polyurethane, epoxy, polyester resin, and/or any material suitable for bonding the fibers to each other and in place. The end of the fibers bound in the potting material may be removed by being cut off in order to expose the hollow ends of the fibers.

In some implementations, the first header piece and the second header piece are further coupled to a first end cap and a second end cap, respectively. The first end cap and the second end cap each have a port that is aligned with the ports on the first and second headers during coupling.

The foregoing is merely illustrative of the principles of the disclosure, and the systems, devices, and methods can be practiced by other than the described embodiments, which are presented for purposes of illustration and not of limitation. It is to be understood that the systems, devices, and methods disclosed herein, while shown for use in high flow therapy systems, may be applied to systems, devices, and methods that require humidification of a gas.

Variations and modifications will occur to those of skill in the art after reviewing this disclosure. The disclosed features may be implemented, in any combination and subcombination (including multiple dependent combinations and subcombinations), with one or more other features described herein. The various features described or illustrated above, including any components thereof, may be combined or integrated in other systems. Moreover, certain features may be omitted or not implemented.

Examples of changes, substitutions, and alterations are ascertainable by one skilled in the art and could be made without departing from the scope of the information disclosed herein. All references cited herein are incorporated by reference in their entirety and made part of this application.

We claim:

1. A vapor transfer cartridge comprising:
   a center tube extending along a first axis from a first end to a second end, having a continuous inner diameter throughout;
   a first header piece coupled to the first end of the center tube, the first header piece configured as a cap and comprising:
      a first channel about an inner circumference of the first header piece and
      a first port for receiving a fluid,
   a plurality of fibers arranged along the first axis of the center tube from the first end to the second end, and
   a second header piece coupled to the second end of the center tube, the second header piece comprising:
      a second port for discharging the fluid and
      a baffle disposed on an interior surface of the vapor transfer cartridge and configured to force the fluid to enter the second port from multiple directions and to prevent the plurality of fibers from being sucked out of the second port.

2. The vapor transfer cartridge of claim 1, further comprising:
   a first end cap coupled to the first header piece, the first end cap comprising a third port; and
   a second end cap coupled to the second header piece, the second end cap comprising a fourth port.

3. The vapor transfer cartridge of claim 2, wherein the first port, the second port, the third port and the fourth port are aligned along a longitudinal axis.

4. The vapor transfer cartridge of claim 3, wherein the first port, the second port, the third port and the fourth port are configured to be attached to a water outlet, a water inlet, an air outlet, and an air inlet, respectively, on a capital unit.

5. The vapor transfer cartridge of claim 4, wherein the third port is configured to receive a gas flow of about 8 lpm when coupled to the air outlet on the capital unit.

6. The vapor transfer cartridge of claim 4, wherein the fourth port is configured to provide a gas with a humidity within the range of 26-56 mg/L to the air inlet on the capital unit.

7. The vapor transfer cartridge of claim 1, wherein the first channel includes one or more ribs configured to align and center the center tube.

8. The vapor transfer cartridge of claim 7, wherein the center tube is configured to be axially adjustable on the ribs to achieve a desired cartridge length.

9. The vapor transfer cartridge of claim 8, wherein the one or more ribs comprises three or more ribs.

10. The vapor transfer cartridge of claim 8, wherein the one or more ribs comprises twelve or more ribs.

11. The vapor transfer cartridge of claim 1, wherein the inner diameter of the center tube is about 28 mm.

12. The vapor transfer cartridge of claim 1, wherein the baffle comprises an outer and an inner longitudinal support and a first and a second lateral support, each support extending from the interior surface toward an interior of the center tube and meeting with a dispersing cap above a baffle opening in fluid connection with the second port, such that the outer and the inner longitudinal support and the first and the second lateral support together with the interior surface form four holes in the baffle.

13. The vapor transfer cartridge of claim 12, wherein the baffle extends into the center tube about 4 mm or less.

14. The vapor transfer cartridge of claim 13, wherein the baffle is configured to provide multi-directional water delivery.

15. The vapor transfer cartridge of claim 1, wherein the second header piece comprises a second channel about an inner circumference of the second header piece, and wherein each of the first header piece and the second header piece includes a sloped region near the first channel and the second channel, respectively, each sloped region configured to center the plurality of fibers.

16. The vapor transfer cartridge of claim 1, wherein each fiber of the plurality of fibers has a diameter of about 0.7 mm.

17. The vapor transfer cartridge of claim 1, wherein the plurality of fibers are porous fibers.

18. The vapor transfer cartridge of claim 1, wherein the plurality of fibers are non-porous fibers.

19. The vapor transfer cartridge of claim 1, wherein the plurality of fibers are configured as hollow fiber tubes.

20. The vapor transfer cartridge of claim 1, wherein the first port includes a barb at an end.

21. A vapor transfer cartridge comprising:
   a center tube extending along a first axis from a first end to a second end, having a continuous inner diameter throughout;
   a first header piece coupled to the first end of the center tube, the first header piece configured as a cap and comprising:
      a first channel about an inner circumference of the first header piece,
      a first port for receiving a fluid, and
      a baffle disposed on an interior surface of the vapor transfer cartridge and configured to disperse the fluid entering the vapor transfer cartridge through the first port,
         the baffle comprising an outer and an inner longitudinal support and a first and a second lateral support, each support extending from the interior surface toward an interior of the center tube and meeting with a dispersing cap above a baffle opening in fluid connection with the first port, such that the outer and the inner longitudinal support and the first and the second lateral support together with the interior surface form four holes in the baffle;
   a plurality of fibers arranged along the first axis of the center tube from the first end to the second end; and
   a second header piece coupled to the second end of the center tube.

* * * * *